United States Patent
Arndt

(10) Patent No.: US 6,893,488 B2
(45) Date of Patent: May 17, 2005

(54) FINGERPRINT COMPOUND AND METHOD

(75) Inventor: Douglas C. Arndt, Jacksonville, FL (US)

(73) Assignee: Armor Holdings Forensics, Inc., Jacksonville, FL (US)

( * ) Notice: Subject to any disclaimer, the term of this patent is extended or adjusted under 35 U.S.C. 154(b) by 0 days.

(21) Appl. No.: 10/620,201

(22) Filed: Jul. 15, 2003

(65) Prior Publication Data

US 2005/0013938 A1 Jan. 20, 2005

(51) Int. Cl.⁷ .............................................. C09D 11/00
(52) U.S. Cl. ............................ 106/31.03; 106/31.01; 106/31.16; 106/31.02; 427/1
(58) Field of Search .................... 108/31.03, 31.01, 108/31.16, 31.02

(56) References Cited

U.S. PATENT DOCUMENTS

| | | | |
|---|---|---|---|
| 4,262,623 A | 4/1981 | Smith, III et al. | |
| 4,705,299 A * | 11/1987 | Hedgcoth et al. | 283/68 |
| 4,879,134 A * | 11/1989 | Vassiliades | 427/1 |
| 4,917,987 A * | 4/1990 | Arndt et al. | 430/139 |
| 4,983,415 A | 1/1991 | Arndt | |
| 5,462,597 A * | 10/1995 | Jubran | 118/31.5 |
| 5,919,292 A | 7/1999 | Arndt | |
| 6,027,556 A | 2/2000 | Arndt | |
| 6,488,750 B1 | 12/2002 | Arndt | |
| 2003/0083199 A1 * | 5/2003 | Arndt | 503/201 |
| 2003/0133958 A1 * | 7/2003 | Kuno et al. | 424/401 |

* cited by examiner

*Primary Examiner*—David Sample
*Assistant Examiner*—Veronica F. Faison
(74) *Attorney, Agent, or Firm*—Harold L. Jackson

(57) ABSTRACT

A printing compound suitable for recording unique surface characteristics of an object such as a person's finger, palm or foot, tire tread or shoe sole, on a porous medium such as paper, is composed of (1) a composition, e.g., printer's ink, capable of delineating such surface characteristics when transferred to the porous medium by itself or in conjunction with a separate reagent and (2) a sufficient amount of water dispersable nonionic surfactant to render the composition substantially soluble in water without adversely affecting the ability of the composition to delineate the surface characteristics when transferred to the porous medium.

30 Claims, No Drawings

FINGERPRINT COMPOUND AND METHOD

FIELD OF THE INVENTION

The present invention relates to the taking of inked impressions from (a) the ridge skin of the fingers, hands, or feet (i.e., dactylographs) or (b) the tread patterns from footwear or vehicular tires. More particularly the invention related to a novel printing compound suitable for taking such impressions and method for taking such impressions.

BACKGROUND OF THE INVENTION

Printer's ink (i.e., a relatively viscous carbon pigmented ink), supplied in a tube and used in conjunction with a roller and plate, has been the preferred medium for decades to record impressions of the fingers, hands, and feet (hereafter referred to as "fingerprints"). A carbon pigmented ink has also been used to record the tread of vehicular tires and the soles of footwear (hereafter collectively referred to as "tread prints"). The shortcoming of these methods is the nature of the ink. Typically, printer's ink is slippery when freshly applied to a plate, which can make inking of the subject difficult. This same difficulty is often experienced when transferring the inked subject to the recording surface, such as paper, in the form of smears or smudges. Printer's ink must be allowed to dry before the document can be handled without damaging the fidelity of the impressions. Printer's ink soils not only the subject, but also the associated tooling and working surfaces. Removal of this ink requires special cleaners or solvents, many of which are hazardous to humans and to the environments and all of which add time and expense to the process. Much ink is wasted because what remains on the roller and plate dries within a brief period and cannot be reused. Over time, the components of printer's ink, may and often do, separate within the packaging, such as a tube, into masses of clear oil and concentrated pigment. This instability impairs the consistency of the fingerprints and tread prints.

The staining problem associated with printer's ink has been overcome to a large extent through the development of inkless or substantially nonstaining inking systems such as those described in U.S. Pat. Nos. 6,488,750 B 1 ("'750 patent"); 6,027,556 ("'556 patent"); 5,919,292 ("'292 patent"); 4,983,415 ("'415 patent") and 4,262,623 ("'623 patent"). Such patents are incorporated herein by reference. While such inkless or nonstaining ink compounds leave little, generally substantially invisible, residue on a person's finger, some clean up is often required.

With respect to the recording of tire tread features, Lawren A. Nause, RCMP, developed a method in which the tire tread surface is coated with a petroleum jelly. The tire is then rolled over a cardboard material. The resulting track left on the cardboard by the petroleum jelly is then developed with a black magnetic latent print powder to obtain a two-dimensional recording of the tire's tread features, i.e., surface characteristics. The record track is then protected by covering it with a clear acetate material. A silicone substance, such as that found in shoeshine sponges, can be substituted for the petroleum jelly and the powdered track protected by the application of a quick drying clear lacquer.

While this method produces clear tire track prints, the powder application and protective covering requirements are time consuming. An alternative method is the preparation of a rather large inking pad containing conventional fingerprint ink and driving the tire over the pad and onto a recording surface. This method requires a large preparation area to accompany both the inking pad and recording surface, which can exceed 14 feet, if an entire rotation of a tire is desired. There is also the added requirement of preparing the large inking pad to transfer a good uniform coating of ink to the tread area. A clean up procedure is also generally required.

A need exists for a printing compound suitable for the above purposes while eliminating many of the shortcomings of the prior art.

SUMMARY OF THE INVENTION

A printing compound suitable for recording unique surface characteristics of an object such as a person's finger, palm or foot or tire tread, on a porous medium, such as paper, comprises an emulsion of (a) a composition capable of delineating such surface characteristics when transferred to the porous medium by itself or in conjunction with a separate reagent and (b) a sufficient amount of water dispersible nonionic surfactant to render the composition substantially soluble in water without adversely affecting the ability of the composition to delineate the surface characteristic when transferred to the porous medium. The compound is thus readily removable from the object through the use of water after the surface characteristics have been recorded.

With respect to a composition consisting of conventional printer's ink, it has been discovered that nonionic surfactants in combination with water-insoluble dispersions of pigment in printer's ink resin can produce a resulting ink paste (compound) that rapidly washes off any non-porous surface with ordinary water alone. Furthermore, this paste remains "wet" substantially indefinitely on the subject and tooling, but is "dry" when applied to a suitable porous recording surface, such as paper. With the proper degree of tack, pitch, and surface tension, smears or smudges are virtually eliminated and damage to the impressions from handling or intentional abuse is virtually eliminated. The fidelity of the fingerprints or tread prints produced by the invention are of such high-quality definition and contrast as to make them well suited for law enforcement and crime scene applications. The ink compound described herein may be reused if desired, requires no cleaning agents other than water, does not separate into its components, and is substantially non-hazardous.

DETAILED DESCRIPTION OF THE INVENTION

The composition of the present invention may be in the form of a carbon pigmented ink, a dye-based ink, or an inkless composition containing one or more reagents. See the above patents. It has been discovered that an oil made water soluble by ethoxylation has the ability to make oil soluble substances miscible in water. It has further been discovered that these ethoxylated oils may be hydrogenated to make them substantially viscous, even to the point of becoming a paste or a soft solid. An example of an ethoxylated, hydrogenated castor oil preferred for the present invention is Lumulse (trademark) GRH-40, manufactured and sold by Lambent Technologies, a Petroferm Company. It is believed that the HLB (Hydrophilic Lipophylic Balance) value of the modified oil, typically a castor oil or other vegetable oil, is the key property that allows water to dissolve hydrophobic materials. The ethoxylation agents are typically polyethylene glycols of various molecular weights and the product often functions as a nonionic surfactant. An ethoxylated oil having a water solubility of about 10 percent or more is sufficient to readily disperse the oleophylic components common to inks.

Nonionic surfactants suitable for use in the invention include ethoxylated sorbitaxi esters, PEG fatty acid esters, ethoxylated glycerin esters, ethoxylated fatty amines, ethoxylated fatty acids, alkoxylated castor oils, ethoxylated alcohols, block ethoxylates/polyoxylates, alkoxylated alcohols, alkoxylated block polymers, ethoxylated alky/phenols, ethoxylated castor glycerides, ethoxylated tall oils and rosin acids, ethoxylated sorbitol fatty acid esters, POE fatty acid ethers, ethoxylated lanolin, ethoxylated hydrogenated lanolin, alkanolamines, fatty alcohol-ethylene oxide condensation products (alkoxylated oils). In general, these are catagorized as water dispersible, nonionic surfactants.

Other alkoxylated oils include the polyethylene glycol esters of jojoba, macadamia, sunflower, coconut, and soy oils. It is preferable to hydrogenate these esters to give them the consistency of a semi-solid a room temperature. The present invention includes the use of nonyl phenol ethoxylates, ethoxylated sorbitan esters such as polyoxyethylene 20 sorbitan monostearate, ethoxylated fatty acids and their esters and amines, and stated generally, nonionic organic surface active agents and ether-esters of polyhydric alcohols. Many of these are approved by the U.S. Food and Drug Administration for use in food, beverage, cosmetic, and personal care products because of their low toxicity and lack of skin irritation characteristics, which makes them ideal for use in fingerprinting compositions.

I found a surprising and unexpected result in formulating printer's ink with, for example, Lumulse GRH-40. The pigment dispersions in printer's ink, e.g., the HW-5400 product manufactured by Wolstenholme International (see the '750 patent), and the thermosetting resins contained therein become instantly soluble in water and substantially non-drying in air. Alkyd resins are thermosetting coating polymers that are completely insoluble in water and can adhere tenaciously to the skin and other surfaces and removal is normally accomplished with hydrocarbon distillates or with polar solvents or the esters thereof. These resins dry upon exposure to air and heat, but fail to do so when combined with the nonionic surfactants as described herein.

Hydrogenation is desirable when the surfactant is in a liquid state and a paste is desired to provide the necessary physical characteristics of pitch and tack.

With respect to recording tread prints any dirt and debris on the tire surface must first be removed, as far as is practical, by wiping the tread area with an absorbent cloth such as a towel. All reachable surface areas should be cleaned. There will be unreachable tread surface in the area where the tire is resting on the road surface and this may be cleaned after the recording procedure is initiated.

A selected piece of cardboard is positioned in front of the mounted tire on the vehicle. If multiple pieces of cardboard are being used, they can be held together by binders or tape. The expected track path should be determined and the cardboard positioned so the tire will roll in the center of the cardboard.

Once the tire surface has been cleaned and the cardboard positioned, the inking of the tire can be started. The glove applicator can be put on like a glove and the inked treated foam is rubbed over all reachable tread area to apply the ink. It is important that the tread area be adequately coated with the ink. The "ink sheen" on the tire surface will show where the ink has been applied. Repeated rubbing over an area to insure full area coverage will not apply excess ink to a tread area. This ink does not dry and will remain fluid until it comes in contact with the recording cardboard.

After all reachable tread area has been inked, the vehicle can be driven or rolled a short distance along the cardboard stock until the tread area of the tire that was not initially reachable is now unobstructed. The rolling action is stopped while this area is cleaned of road debris and ink applied to this area of the tread, making sure the ink overlaps the previously applied areas.

When the entire area of the tire tread has been inked, the recording procedure can continue by driving or rolling the vehicle to obtain a full rotation of the tire. Once a piece of the cardboard has been driven over, it can be removed if there is a concern of it being overdriven by a trailing tire. However, if accidentally overdriven, there should be no adverse effect on the already inked recording of the leading tire.

It is expected that examiners of tire track evidence, which require a full rotation of a tire, to conduct a comparative examination between a questioned track and a suspect tire will employ this recording method. However, this technique can also be considered whenever partial tire design recordings may be needed for investigative purposes.

Shoe prints can be recorded in a similar manner. Once the shoe bottom has been cleaned of debris the printing compound, e.g., an emulsion of printer's ink and the nonionic surfactant, may be applied thereto and the shoe bottom then pressed against the recording medium such as paper.

EXAMPLES OF A PRINTING COMPOUND IN ACCORDANCE WITH THE INVENTION

Example 1

Pigmented fingerprint ink—by weight, 3 parts Lambents Technology's Lumulse GRH-40, 1 part Wolstenholme International's HW-5400 black base. A black, non-drying paste suitable for use as a fingerprinting ink packaged in a tube was produced. The product rinsed completely from the fingers and related equipment using only tap water. The inked impressions of the fingers were instantly non-smearing and "dry" on the recording paper be means of absorption. The impressions exhibited excellent contrast and clarity. The residual ink left on the roller and plate could be used three months later just as if it were freshly applied.

Example 2

Pigmented tread ink—1400 grams Lambent Technology's Lumulse GRH-40, 560 grams either isopropyl myristate or capric/caprylic triglyceride, 280 grams Wolstemholme International's HW-5400 black base. A black, viscous, non-drying ink suitable for impregnation into reticulated polyester foam pads was produced. Impressions of automotive tires and of the soles of shoe were obtained that exhibited fine details of tread and wear patterns. These impressions were instantly "dry" and tamper-proof upon the poster board, recording surface. The ink rinsed away readily from the rubber surfaces subjects using tap water alone.

Example 3

A paste was produced having all of the properties of the product of Example 1 by substituting Lumulse GRH-40 with Lambent Technology's Lumisorb (trademark) PSMS-20, a polysorbate 60.

Example 4

Inkless reagent ('415 patent)—2380 grams Lambent Technology's Lumulse GRH-40, 143.83 grams propylene glycol, 933.33 grams ferric chloride hexahydrate. A viscous solution was produced that could be impregnated into a porous plastic or a porous ceramic pad. This reagent produced high-contrast, high resolution, black fingerprint and tread print images on thermo-sensitive paper. This reagent could also be rolled out onto a glass plate to achieve the same results.

Example 5

Single-phase inkless reagent ('750 patent)—500 grams Lambent Technology's Lumulse GRH-40, 400 grams polyoxyl 40 stearate, 100 milliliters propylene glycol, 45 grams ferric chloride hexahydrate, 32 grams citric acid, 72.6 grams 8-hydroxyquinoline. A pale paste was formed that could be flexographically printed onto synthetic paper as fields of reagent to produce "inking" foils. The fingerprints were dark gray and non-smearing. The reagent was virtually non-staining to the fingers and the minute amount of residue was easily washed off with water.

Example 6

Pigmented ink paste—by weight, 70% Lambent Technology's Lumulse GRH-40, 20% anhydrous lanolin, 10% electrostatic copier toner. The results were similar to those of Example 1.

Example 7

Dye-based ink ('556 patent)—600 grams Lambent Technology's Lumulse GRH-40, 400 grams polyethylene glycol 200, 40 grams nigrosine base. This viscous ink produced bluish black impressions having high contrast and clarity. These results were obtained from a polyvinylchloride pad comprised of reticulated microcells. Similar results were obtained from a single layer of melt-blown polyester affixed to a polymer-laminated foil as described in patent 6,027,556 by the inventor. The result that the dye was instantly washable from the fingers without having to rub the fingers together or without the use of a towel, but by rinsing with tap water alone, was unexpected.

There has thus been disclosed several examples of the present invention which overcomes many of the problems of the prior art. It is to be noted that the invention is not limited to such examples and that the spirit and scope of the present invention is defined by the appended claims.

What is claimed is:

1. A printing compound suitable for recording the unique surface characteristics of an object such as a person's fingerprint area, a tire tread or shoe sole on a porous medium such as paper comprising an emulsion of:
   a composition capable of delineating the surface characteristics when transferred from the object's surface to the porous medium by itself or in conjunction with a separate reagent; and
   a sufficient amount of a water dispersable nonionic surfactant to render the composition substantially soluble in water whereby the composition may be readily removed from the object through the use of water after the surface characteristics thereon have been recorded.

2. The printing compound of claim 1 wherein the nonionic surfactant contains an ethoxylated oil.

3. The printing compound of claim 2 wherein the ethoxylated oil is hydrogenated.

4. The printing compound of claim 3 wherein the oil is a vegetable oil.

5. The printing compound of claim 4 wherein the vegetable oil is castor oil.

6. The printing compound of claim 2 wherein the ethoxylated oil is a PEG-40 castor oil ester.

7. The printing compound of claim 3 wherein the hydrogenated oil is a PEG-40 ester.

8. The printing compound of claim 1 wherein the nonionic surfactant is GRI-40.

9. The printing compound of claim 1 wherein the nonionic surfactant is alkoxylated oil.

10. The printing compound of claim 1 wherein the composition is printer's ink.

11. The printing compound of claim 1 wherein the composition is an inkless reagent containing one or more metallic salts in solution.

12. The printing compound of claim 1 wherein the composition is an inkless fingerprint compound containing in solution a color former, a developer capable of reacting with the color former to form a colorant product and a sufficient amount of chelating agent to substantially prevent the color former and developer from reacting while in solution while permitting such reaction when the solution is applied to a person's fingerprint area and deposited onto a porous substrate.

13. The printing compound of claim 1 wherein the composition is a dye based ink comprising one or more alcohol dyes and one or more fatty acid esters.

14. The printing compound of claim 1 wherein the nonionic surfactant is selected from one or more of the group consisting of ethoxylated polyethylene/polypropylene glycols, ethoxylated sorbitan esters, PEG fatty acid esters, ethoxylated glycerin esters, ethoxylated fatty amines, ethoxylated fatty acids, alkoxylated castor oils, ethoxylated alcohols, block ethoxylates/polyoxylates, alkoxylated alcohols, alkoxylated block polymers, ethoxylated alky phenols, ethoxylated castor glycerides, ethoxylated tall oils and rosin acids, ethoxylated sorbitol fatty acid esters, POE fatty acid ethers, ethoxylated lanolin, ethoxylated hydrogenated lanolin, alkanolamines, fatty alcohol-ethylene oxide condensation products (alkylated oils).

15. A fingerprint ink compound comprising an emulsion of:
   printer's ink; and
   a sufficient amount of a water dispersable nonionic surfactant to render the printer's ink substantially soluble in water without adversely affecting the ability of the printer's sink to delineate the surface characteristics when transferred to the porous medium.

16. The fingerprint ink of claim 15 wherein the surfactant contains an ethoxylated oil.

17. The printing compound of claim 16 wherein the ethoxylated oil is hydrogenated.

18. The printing compound of claim 17 wherein the oil is a vegetable oil.

19. The printing compound of claim 18 wherein the vegetable oil is castor oil.

20. The printing compound of claim 16 wherein the ethoxylated oil is a PEG-40 castor oil ester.

21. The printing compound of claim 15 wherein the hydrogenated oil is a PEG-40 ester.

22. The printing compound of claim 15 wherein the nonionic surfactant is GRH-40.

23. The printing compound of claim 15 wherein the nonionic surfactant is selected from one or more of the group consisting of ethoxylated polyethylene/propylene glycols, ethoxylated sorbitan esters, PEG fatty acid esters, ethoxylated glycerin esters, ethoxylated fatty amines, ethoxylated fatty acids, alkoxylated castor oils, ethoxylated alcohols, block ethoxylates/polyoxylates, alkoxylated alcohols, alkoxylated block polymers, ethoxylated alky phenols, ethoxylated castor glycerides, ethoxylated tall oils and rosin acids, ethoxylated sorbitol fatty acid esters, POE fatty acid ethers, ethoxylated lanolin, ethoxylated hydrogenated lanolin, alkanolamines, fatty alcohol-ethylene oxide condensation products (alkylated oils).

24. The printing compound of claim 16 wherein ethoxylated oil has a water solubility of about 10% or more.

25. A method of taking an inked impression of the unique surface characteristics of an object comprising:
 a) providing an emulsion ofa composition capable of delineating such surface characteristics when transferred from the object's surface to a porous medium by itself or in conjunction with a separate reagent and a sufficient amount of a water dispersable nonionic surfactant to render the composition substantially soluble in water without substantially affecting the ability of the composition to delineate the surface characteristics when transferred to the porous medium;
 b) coating the desired surface of the object with the emulsion; and
 c) pressing the desired surface of the object against a porous recording medium.

26. The method of claim 25 further including the step of applying water to the object's surface to remove the emulsion therefrom.

27. The method of claim 25 wherein the object is a tire, the composition is printer's ink, the coating step comprises using a hand applicator to apply the emulsion to the tread surface of the tire and the pressing step comprises rolling the tire over the recording medium.

28. The method of claim 27 wherein the recording medium is paper.

29. The method of claim 25 wherein the object is the bottom of a shoe, the composition is printer's sink, the coating step comprises using a hand applicator to apply the emulsion to the bottom of the shoe and the pressing step comprises forcing the bottom of the shoe against the recording medium.

30. The method of claim 29 wherein the recording medium is paper.

* * * * *

UNITED STATES PATENT AND TRADEMARK OFFICE
CERTIFICATE OF CORRECTION

PATENT NO. : 6,893,488 B2
DATED : May 17, 2005
INVENTOR(S) : Arndt

It is certified that error appears in the above-identified patent and that said Letters Patent is hereby corrected as shown below:

Column 3,
Line 4, "sorbitaxi" should read -- sorbitan --.

Column 6,
Line 6, "GRI-40" should read -- GRH-40 --.

Column 7,
Line 11, "ofa" should read -- of a --.

Column 8,
Line 14, "sink" should read -- ink --.

Signed and Sealed this

Nineteenth Day of July, 2005

JON W. DUDAS
*Director of the United States Patent and Trademark Office*